United States Patent [19]

Hartwig et al.

[11] Patent Number: 5,817,877
[45] Date of Patent: Oct. 6, 1998

[54] METAL-CATALYZED AMINATION OF ORGANIC SULFONATES TO ORGANIC AMINES

[75] Inventors: John F. Hartwig, New Haven, Conn.; Michael S. Driver, Redwood City, Calif.; Janis Louie; Blake Hamann, both of New Haven, Conn.

[73] Assignee: Yale University, New Haven, Conn.

[21] Appl. No.: 933,658

[22] Filed: Sep. 19, 1997

Related U.S. Application Data

[60] Provisional application No. 60/025,767, Sep. 23, 1996.

[51] Int. Cl.[6] .................................................. C07C 209/22
[52] U.S. Cl. .......................... 564/399; 544/163; 544/178; 546/192; 546/205; 558/422; 564/396; 564/408
[58] Field of Search ..................................... 544/163, 178; 558/422; 564/396, 399, 408; 546/205, 192

[56] References Cited

U.S. PATENT DOCUMENTS 5,576,460  11/1996  Buchwald et al. ....................... 564/386

OTHER PUBLICATIONS

J. P. Wolfe and S. L. Buchwald, "Palladium–Catalyzed Amination of Aryl Triflates," *Journal of the American Chemical Society*, 62 (No. 5), 1997, 1264–1267.

J. Louie and J. F. Hartwig, "Palladium–Catalyzed Synthesis of Arylamines from Aryl Halides. Mechanistic Studies Lead to Coupling in the Absence of Tin Reagents," *Tetrahedron Letters*, 36 (No. 21), 1995, 3609–3612.

J. Louie, M. S. Driver, B. C. Hamann, and J. F. Hartwig, "Palladium–Catalyzed Amination of Aryl Triflates and Importance of Triflate Addition Rate," *Journal of Organic Chemistry*, 62 (No. 5), 1997, 1268–1273.

H. Kotsuki et al., "High Pressure Organic Chemistry; XI. A New Convenient Synthesis of Aromatic Amines from Activated Phenols," *Synthesis*, Dec. 1990, 1145–1146.

J. P. Wolfe, R. A. Rennels, and S. L. Buchwald, "Intramolecular Palladium–Catalyzed Aryl Amination and Aryl Amidation," *Tetrahedron*, 52 (No. 21), 1996, 7525–7546.

M. S. Driver and J. F. Hartwig, "A Second Generation Catalyst for Aryl Halide Amination: Mixed Secondary Amines from Aryl Halides and Primary Amines Catalyzed by (DPPF)PdCl$_2$," *Journal of the American Chemical Society*, 118 (No. 30), 1996, 7217–7218.

J. P. Wolfe et al., "An Improved Catalyst System for Aromatic Carbon–Nitrogen Bond Formation: The Possible Involvement of Bis(Phosphine)Palladium Complexes as Key Intermediates," *Journal of the American Chemical Society, Communications*, 118 (No. 30), 1996, 7215–7216.

J. P. Wolfe and S. L. Buchwald, "Palladium–Catalyzed Amination of Aryl Iodides," *Journal of Organic Chemistry*, 61 (No. 3), 1996, 1133–1135.

A. S. Guram et al., "A Simple Catalytic Method for the Conversion of Aryl Bromides to Arylamines," *Angew. Chem. Int. Ed. Engl.*, 34 (No. 12), 1995, 1348–1350.

V. Farina et al., "Palladium–Catalyzed Coupling of Arylstannanes with Organic Sulfonates: A Comprehensive Study," *Journal of Organic Chemistry*, 58 (No. 20), 1993, 5434–5444.

Ng Ph. Buu–Hoi, "The Scope of the Knoevenagel Synthesis of Aromatic Secondary Amines," *Journal of the Chemical Society*, 1952, 4346–4349.

R. A. Rossi and J. F. Bunnett, "A General Conversion of Phenols to Anilines," *Journal of Organic Chemistry, Communications*, 37 (1972), 3570.

H. Seeboth, "The Bucherer Reaction and the Preparative Use of its Intermediate Products," *Angew. Chem. International Edition*, 6 (No. 4), 1967, 307–317.

*Primary Examiner*—Brian M. Burn
*Attorney, Agent, or Firm*—Marie F. Zuckerman

[57] ABSTRACT

A process of preparing an organic amine having at least one unsaturated group, such as an arylamine, involving contacting an unsaturated organic sulfonate, such as an aryl sulfonate, with a reactant amine, such as an alkyl or aryl amine, in the presence of a base and a transition metal catalyst under reaction conditions. The transition metal catalyst contains a Group 8 metal and a chelating ligand, for example a Group 15-substituted arylene or Group 15-substituted metallocene, such as 1,1'-bis (diphenylphosphino)-2,2'-binaphthyl or 1,1'-bis (diphenylphosphino)-ferrocene, respectively. The aryl sulfonate can be prepared from a phenol and sulfonating agent.

31 Claims, No Drawings

METAL-CATALYZED AMINATION OF ORGANIC SULFONATES TO ORGANIC AMINES

This application was made with United States Government support under Award Number CHE-9457672 awarded by The National Science Foundation.

This application claims the benefit of U.S. Provisional application Ser. No. 60/025,767, filed Sep. 23, 1996.

BACKGROUND OF THE INVENTION

This invention pertains to a process of preparing organic amines containing at least one unsaturated group, such as arylamines, from unsaturated organic sulfonates, such as aryl sulfonates. In another aspect, this invention pertains to a process of preparing arylamines starting from phenols and using organic sulfonates as intermediates.

Arylamines and heteroaryl amines are important substructures in natural products and industrial chemicals, such as pharmaceuticals, dyes, and agricultural products. Arylpiperazines, for example, and carbazoles, indoles, and pyrroles are known to exhibit pharmacological activity. Naphthylamines are important as dye intermediates. Arylamines and vinylamines find utility in the synthesis of polymers and oligomers. The conversion of phenols to phenylamines could be useful in the modification of biologically important compounds, such as tyrosine and tyrosine-containing peptides.

It would be advantageous to prepare arylamines from phenols, because phenols are inexpensive and readily available. To date, methods designed along these lines are inefficient or economically unattractive. For example, the iodine-catalyzed condensation of phenols with primary aromatic amines to form secondary aromatic amines has been disclosed by Ng. Ph. Buu-Hoi in the *Journal of the Chemical Society,* 1952, 4346–4349. This process disadvantageously requires high temperatures.

An alternative synthesis of arylamines has been disclosed which involves converting a phenol to an aryl phosphate, and thereafter, converting the aryl phosphate to the arylamine. For a representative disclosure, see R. Rossi and J. F. Bunnett, *Journal of Organic Chemistry, Communications,* 37 (1972), 3570. Disadvantageously, the conversion of the aryl phosphate to the arylamine requires potassium metal and liquid ammonia.

The Bucherer reaction has also been disclosed for converting specific hydroxyaromatic compounds into primary, secondary, and tertiary aromatic amines. This reaction proceeds in an aqueous phase in the presence of a reactant amine and sulfurous acid or its salts. A representative disclosure is given by H. Seeboth, *Angewante Chemie, International Edition,* 6 (1967), 307–317. Disadvantageously, the Bucherer reaction is limited to the conversion of naphthols to naphthylamines.

From a different starting point, arylamines have been taught to be prepared by converting a phenol to an aryl sulfonate and thereafter converting the aryl sulfonate to an arylamine, as found in the publication of H. Kotsuki et al., *Synthesis,* 1990, 1145–1146. It is disclosed that phenol reacts with triflic anhydride to form an aryl triflate which reacts with a primary or secondary amine to yield an arylamine. This reference is silent with respect to the use of a catalyst for the conversion of the aryl triflate to the arylamine. Disadvantageously, the process is limited to aryl sulfonates containing a strong electrophilic substituent, such as nitro or fluorine. The process is more disadvantageous in its use of high pressures.

In view of the above, a need exists for a general and efficient process of synthesizing an arylamine from a phenol or an aryl sulfonate. The discovery of such a method would simplify the preparation of commercially significant organic amines and would enhance the development of novel pharmacologically active arylamines.

SUMMARY OF THE INVENTION

This invention is a process of preparing an organic amine containing at least one unsaturated organic group. The process comprises contacting an unsaturated organic sulfonate with a reactant amine in the presence of a base and a transition metal catalyst under reaction conditions sufficient to prepare an organic amine containing at least one unsaturated organic group. The transition metal catalyst comprises a Group 8 metal and at least one chelating ligand containing an element from Group 15 of the Periodic Table of the Elements. The Periodic Table referred to herein is The Periodic Table referenced in the *CRC Handbook of Chemistry and Physics,* 75th ed., CRC Press, 1994–1995. More particularly, the chelating ligand is selected from the group consisting of unsaturated Group 15 heterocycles, Group 15-substituted arylenes, Group 15-substituted metallocenes, and Group 15-substituted alkanes, each group described hereinafter.

The process of this invention beneficially produces an organic amine containing at least one unsaturated group directly from an unsaturated organic sulfonate and a reactant amine. Advantageously, the process of this invention can be conducted under mild reactions conditions. More advantageously, the process of this invention avoids the use of organic halides which may be corrosive. Even more advantageously, the process of this invention produces good yields of the organic amine product.

In another aspect, this invention is a process of preparing an arylamine from a phenol. The process comprises (a) contacting a phenol with a sulfonating agent under reaction conditions sufficient to prepare an aryl sulfonate, and thereafter (b) contacting the aryl sulfonate with a reactant amine in the presence of a base and a transition metal catalyst under reaction conditions sufficient to prepare the arylamine. The transition metal catalyst comprises a Group 8 metal and at least one chelating ligand containing an element from Group 15 of the Periodic Table of the Elements. More particularly, the chelating ligand is selected from the group consisting of unsaturated Group 15 heterocycles, Group 15-substituted arylenes, Group 15-substituted metallocenes, and Group 15-substituted alkanes.

The aforementioned process of this invention beneficially converts a phenol into an arylamine via an aryl sulfonate intermediate. Typically, phenols are inexpensive and readily available; therefore, the use of phenols as the starting point for the synthesis of arylamines is particularly advantageous. As an added advantage, the invention provides a general and efficient route to arylamines which find utility in the syntheses of commercially important pharmaceuticals, agricultural chemicals, polymers, and dyes.

DETAILED DESCRIPTION OF THE INVENTION

The process of this invention involves the synthesis of organic amines containing at least one unsaturated group, specifically a vinyl, aryl, or heteroaryl group. The process comprises contacting an unsaturated organic sulfonate with a reactant amine in the presence of a base and a transition metal catalyst under reaction conditions sufficient to prepare the organic amine containing at least one unsaturated group. The transition metal catalyst comprises a Group 8 metal and at least one chelating ligand containing an element from Group 15 of the Periodic Table of the Elements. More specifically, the chelating ligand is selected from the group consisting of unsaturated Group 15 heterocycles, Group 15-substituted arylenes, Group 15-substituted metallocenes, and Group 15-substituted alkanes.

More specifically, the process of this invention can be represented by

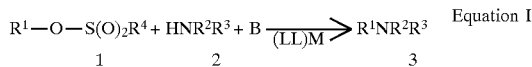 Equation I wherein <u>1</u> represents the unsaturated organic sulfonate, <u>2</u> represents the reactant amine, B represents the base, (LL)M represents the catalyst comprising chelating ligand (LL) and Group 8 metal (M), and <u>3</u> represents the organic amine product having at least one unsaturated organic group. Each of the species <u>1</u>, <u>2</u>, <u>3</u>, B and (LL)M are described in detail hereinafter. In addition to the amine product (<u>3</u>), it is believed that the product mixture contains the base in its conjugate acid form (BH) and contains the sulfonate ion [O-S(O)$_2$R$^4$] as a salt. Such a theory, however, should not be limiting or binding upon the invention in any manner.

In a preferred embodiment of this invention, an aryl sulfonate or heteroaryl sulfonate is employed in the process of this invention to prepare an arylamine or heteroarylamine, respectively. In a more preferred embodiment of this invention, a phenyl sulfonate is employed in the process of this invention to prepare a phenylamine.

The unsaturated organic sulfonate (<u>1</u>) can be any organic sulfonate containing an unsaturated group R$^1$. For the purposes of this invention, the term "unsaturated group", as used herein, includes vinyl groups, aromatic groups, such as phenyl and naphthyl; and heteroaryl groups, such as furyl. Preferably, R$^1$ is a $C_{2-20}$ vinyl, $C_{5-15}$ aryl, or $C_{4-15}$ nitrogen, oxygen, or sulfur-containing heteroaryl group. Examples of suitable vinylic groups include, but are not limited to, vinyl, 1-propenyl, 1-methylvinyl, 1-butenyl, 1-pentenyl, 1-cyclohexenyl, and the like, as well as phenyl-substituted vinylic groups, such as styryl. Examples of suitable aryl groups include five, six, seven, and eight-membered monocyclic aromatic groups, such as phenyl, cumenyl, tolyl, xylyl, and cyclopentadienyl; polyaryl ring assemblies, such as biphenylyl and terphenylyl; and groups derived from fused aromatic rings, such as naphthyl, indenyl, anthryl, phenanthryl, azulenyl, fluorenyl, and phenalenyl. R$^1$ substituents derived from nitrogen, oxygen, and sulfur-containing heterocycles having vinylic or aromatic character may also be employed. Accordingly, non-limiting examples of R$^1$ may also include furyl, pyranyl, isobenzofuranyl, xanthenyl, pyridyl, pyrazinyl, pyrimidinyl, pyrrolyl, indolizinyl, isoquinolyl, quinolyl, thienyl, benzothienyl, naphthothienyl, and thianthrenyl.

Any of the vinyl, aryl, or heteroaryl R$^1$ groups mentioned hereinabove may be substituted with one or more inert substituents, that is, substituents which are substantially non-reactive in the process of this invention. Non-limiting examples of suitable inert substituents include alkoxy, acyl, ester, silyl ether, secondary and tertiary amino, chloro, fluoro, and cyano groups.

The unsaturated organic sulfonate (<u>1</u>) is also characterized by substituent R$^4$ which may be any group which provides a reactive sulfonate in the process of this invention. Non-limiting examples of R$^4$ broadly include alkyl, perfluoroalkyl, aryl, and alkaryl groups. Preferably, R$^4$ is selected from the group consisting of $C_{1-10}$ alkyl, $C_{1-10}$ perfluoroalkyl, $C_{6-15}$ aryl, and $C_{6-15}$ alkaryl groups. More preferably, R$^4$ is selected from the group consisting of methyl, trifluoromethyl, perfluorobutyl, phenyl, and tosyl groups. Accordingly, the more preferred organic sulfonates are methylates, triflates, nonaflates, phenylates, and tosylates, respectively. Even more preferably, the unsaturated organic sulfonate is an $C_{5-15}$ aryl triflate or $C_{4-15}$ heteroaryl triflate. Most preferably, the organic sulfonate is an aryl triflate selected from the group consisting of 4-methoxyphenyl triflate, 2-naphthyl triflate, 4-cyanophenyl triflate, 4-benzoylphenyl triflate, 4-phenylphenyl triflate, and 2-methylphenyl triflate.

Any reactant amine can be employed in the process of this invention provided that the process yields an organic amine product containing at least one unsaturated moiety. The reactant amine can be ammonia, or alternatively, a primary or secondary organic amine. Suitably, the amine may be represented by formula 2 hereinabove wherein R$^2$ and R$^3$ are each independently selected from the group consisting of hydrogen, alkyl, cycloalkyl, and aryl groups. Alteratively, R$^2$ and R$^3$ may together with the nitrogen atom of the reactant amine form a saturated or unsaturated heterocycle. Each of R$^2$ and R$^3$ can be substituted with one or more inert substituents, by which it is meant that the substituent(s) are substantially non-reactive and do not inhibit the process of this invention. Non-limiting examples of suitable substituents include cyano, chloro, fluoro, ether, acyl, secondary and tertiary amino, and silyl ether groups. Examples of reactant amines which can be beneficially employed in the process of this invention include, but are not limited to, ammonia, ethylamine, propylamine, n-butylamine, t-butylamine, pentylamine, hexylamine, cyclohexylamine, octylamine, 2-ethylhexylamine, dipropylamine, dibutylamine, dicyclohexylamine, cyclohexylethylamine, aniline, toluidine, dimethylaniline, isopropylaniline, N-methylaniline, N,N-diphenylamine, morpholine, isoindoline, indoline, piperazine, piperidine, pyrazoline, pyrazolidine, imidazoline, imidazolidine, pyrroline, pyrrolidine, phenoxazine, carbazole, purine, indole, isoindole, pyrrole, pyrazole, and imidazole. Preferably, R$^2$ and R$^3$ are each independently selected from the group consisting of hydrogen, $C_{1-20}$ alkyl, $C_{4-8}$ cycloalkyl, and $C_{6-15}$ aryl groups. In an alternative preferred embodiment, R$^2$ and R$^3$ together with the nitrogen of the reactant amine form a $C_{4-15}$ saturated or unsaturated heterocycle. More preferably, the reactant amine is piperidine, aniline, morpholine, piperazine, carbazole, indole, or pyrrole.

Insofar as the discussion is concerned hereinabove, the unsaturated organic sulfonate and the reactant amine exist as two separate molecules. In this situation the process can be interpreted as an intermolecular reaction. The process, however, is not limited solely to intermolecular reactions. Under different circumstances the process can occur as an intramolecular reaction. Such is the case when both the sulfonate and amine functionalities are attached to the same molecule, for example, when the unsaturated organic sulfonate also contains an aminoalkyl moiety, generally in an ortho arrangement. In this situation the process proceeds as an intramolecular cyclization, and typical reaction products include five, six, and seven-membered ring N-heterocycles. As an example of an intramolecular process of this invention, o-aminoethylphenyl sulfonate can be converted under the process conditions to indoline.

The quantities of unsaturated organic sulfonate and reactant amine which are employed in the process of this invention may be any quantities which provide for an organic amine having at least one unsaturated group as a product. The reactant amine may be used in a molar excess or molar deficiency relative to the unsaturated organic sulfonate. The economics of the reagents frequently determines whether an excess or deficiency of reactant amine is used. Typically, the molar ratio of reactant amine to unsaturated organic sulfonate ranges from about 1/1 to about 10/1. Preferably, the molar ratio of reactant amine to unsaturated organic sulfonate ranges from about 1.1/1 to about 5.0/1

A base, designated "B" in Equation I, is required for the process of this invention. Any base may be used so long as the process proceeds to the organic amine product having at least one unsaturated organic group. It may be important in this regard that the base does not displace all of the chelating ligands on the catalyst. Nuclear magnetic resonance spectroscopy, infrared, and Raman spectroscopies, for example, are useful in determining whether the chelating ligands remain bonded to the Group 8 metal or whether the ligands have been displaced by the base. Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethylammonium hydroxide and tetraethyl-ammonium hydroxide; and diaza organic bases, such as 1,8-diazabicyclo-[5.4.0.]-undec-7-ene and 1,8-diazabicyclo-[2.2.2]-octane. Preferably, the base is an alkali hydroxide or alkali alkoxide, more preferably, an alkali alkoxide, and most preferably, an alkali metal $C_{1-10}$ alkoxide.

The quantity of base which is used can be any quantity which allows for the formation of the organic amine product. Preferably, the molar ratio of base to unsaturated organic sulfonate ranges from about 1/1 to about 3/1, and more preferably between about 1/1 and about 2/1.

The catalyst, designated (LL)M in Equation I, is characterized as comprising a metal atom or ion (M) and at least one or more chelating ligands (LL). The metal atom or ion is required to be a Group 8 transition metal, that is, a metal selected from iron, cobalt, nickel, ruthenium, rhodium, palladium, osmium, iridium, and platinum. Preferably, the Group 8 metal is palladium, platinum, or nickel, more preferably, palladium. The Group 8 metal may exist in any oxidation state ranging from the zerovalent state to any higher valence available to the metal.

The chelating ligand may be a neutral molecule or charged ion. A chelating ligand possesses a plurality of coordination sites, typically two, three, or four. Preferably, the chelating ligand is a bidentate ligand, that is, one having two coordination sites. The chelating ligand is also required to contain at least one element from Group 15 of the Periodic Table, preferably, at least one element of nitrogen, phosphorus, or arsenic, more preferably, nitrogen or phosphorus. If only one of the Group 15 elements is present, then at least a second chelating element is required, for example, oxygen or sulfur. More specifically, the chelating ligand is selected from the group consisting of unsaturated Group 15 heterocycles, Group 15-substituted arylenes, Group 15-substituted metallocenes, and Group 15-substituted alkanes.

The term "unsaturated Group 15 heterocycles" as used herein includes any unsaturated single ring, multiple ring assembly, or fused ring system which comprises at least one Group 15 heteroatom. Preferably, the heteroatom is nitrogen. Chelating atoms outside of Group 15, such as oxygen or sulfur, may also be present. Non-limiting examples of unsaturated Group 15 heterocycles which are chelating and which can be beneficially employed in the process of this invention include bipyridine, alkoxypyridine, imidazole, pyrazole, pyrimidine, pyridazine, purine, and quinazoline. Preferably, the unsaturated Group 15 heterocycle is an unsaturated $C_{5-15}$ Group 15 heterocycle, more preferably, bipyridine or alkoxypyridine.

The term "Group 15-substituted arylenes" as used herein includes aromatic compounds substituted with at least one Group 15-containing moiety, preferably, at least one dialkyl or diaryl Group 15 moiety or hybrid thereof. The aromatic compound can be a single ring, fused ring, or multiple ring assembly. Other chelating elements, such as oxygen or sulfur, may be present. Non-limiting examples of Group 15-substituted arylenes which are chelating and beneficially employed in the process of this invention include 1,2-bis(diphenylphosphino)benzene, 1,1'-bis(diphenylphosphino)-2,2'-binaphthyl, 1-(dimethylarsino)-2-bis[(dimethylamino)phosphino]benzene, 1,2-bis(dimethylarsino)benzene, 5,10-dihydro-5,10-diphenyl-5-phospha- 10-arsa-anthracene, 2-diphenylphosphino-N,N-dimethylaniline, 1,8-bis(diphenylphosphino)naphthalene, 2-2'-bis(diphenylphosphino)diphenyl ether, 4,5-bis(diphenylphosphino)-9,9-(dimethyl)xanthene, and 1,1'-bis(di-p-tolylphosphino)-2,2'-binaphthyl. Analogous diamino, diphosphino, and diarsino compounds and hybrids thereof are also suitable. Preferably, the Group 15-substituted arylene is a Group 15-substituted $C_{4-20}$ arylene, more preferably, a Group 15-substituted binaphthyl compound, more preferably, 1,1'-bis(diphenylphosphino)-2,2'-binaphthyl (BINAP) or 1,1'-bis(di-p-tolylphosphino)-2,2'-binaphthyl.

The term "Group 15-substituted metallocenes" as used herein includes metallocenes which are substituted with at least one Group 15-containing moiety, preferably, at least one dialkyl or diaryl Group 15 moiety or hybrid thereof. Other chelating elements, for example, oxygen or sulfur, may be present. The metallocene, itself, comprises a transition metal atom or ion which is bonded to one or more $C_{4-8}$ multiply unsaturated hydrocarbon ring compounds. Suitable non-limiting examples of transition metal atoms in the metallocene include iron, titanium, vanadium, chromium, manganese, cobalt, nickel, molybdenum, and ruthenium. Preferably, the transition metal atom in the metallocene is iron. The $C_{4-8}$ multiply unsaturated hydrocarbon ring compounds suitably include cyclobutadiene, cyclopentadienyl, benzene, cycloheptatrienyl, and cyclooctatetraene. Representative metallocenes include ferrocene, ruthenocene, bis(benzene)chromium, bis(benzene)molybdenum, bis(benzene)tungsten, and cobaltocenium. Non-limiting examples of ligands which classify as chelating Group 15-substituted metallocenes include 1,1'-bis(diphenylphosphino)ferrocene, 1-diphenylphosphino-2-(1-dimethylamino)ethyl ferrocene, 1-diphenylarsino-1'-diphenylphosphino ferrocene, and analogous phosphine and amine substituted derivatives of the aforementioned metallocenes. Preferably, the Group 15-substituted metallocene is a Group 15-substituted ferrocene, more preferably, 1,1'-bis(diphenylphosphino)ferrocene (DPPF).

The term "Group 15-substituted alkanes" as used herein includes alkanes, preferably $C_{2-5}$ alkanes, and more preferably $C_{3-4}$ alkanes, which are substituted with at least one Group 15-containing moiety, preferably, a dialkyl or diaryl Group 15 moiety or hybrid thereof. Non-limiting examples of ligands which classify as chelating Group 15-substituted alkanes and which may be beneficially employed in the process of this invention include 1,3-bis(diphenylphosphino)propane, 1,4-bis(diphenylphosphino)butane, 1,3-bis(diphenylarsino)propane, 1,4-bis(diphenylarsino)butane, 1-(diphenylphosphino)-2-(N,N-dimethyl)ethane, 1-(diphenylphosphino)-3-(N,N-dimethyl)propane, and 1-(diphenylarsino)-2-(diphenylphosphino)ethane.

In one preferred embodiment, the chelating ligand is a bidentate ligand containing at least one phosphorus atom. More preferably, the chelating ligand is a bidentate ligand selected from the group consisting of phosphorus-substituted arylenes and phosphorus-substituted metallocenes. Most preferably, the ligand is 1,1'-bis(diphenylphosphino)-2,2'-binaphthyl (BINAP), 1,1'-bis(di-p-tolylphosphino)-2,2'-binaphthyl (Tol-BINAP), or 1,1'-bis(diphenylphosphino)ferrocene (DPPF).

Many of the aforementioned ligands can be purchased; others can be synthesized by methods available to those skilled in the art.

The preferred transition metal catalysts which are beneficially employed in the process of this invention can be represented by the following formula:

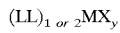

$$(LL)_{1 \text{ or } 2}MX_y$$

wherein (LL) is the chelating ligand, M is the Group 8 transition metal, each X is independently a monovalent anionic ligand, including for example a halide, such as chloride; a carboxylate, such as acetate; or an alkyl sulfonate, such as triflate; or X is a divalent anionic ligand, such as sulfonate or carbonate; and wherein y represents the total number of anionic ligands X required to balance charge, typically from 0 to about 4. The following non-limiting examples of suitable transition metal complexes are offered: dichloro-[1,1'-bis(diphenylphosphino)ferrocene]palladium (II), dichloro-[1,1'-bis(diphenylphosphino)-2,2'-binaphthyl]palladium (II), dichloro-[1,2-bis(diphenylarsino)benzene]platinum (II), 1,2-bis[(diphenylphosphino)benzene]platinum (II) acetate, dichloro-[1-diphenylphosphino-2-(1-dimethylamino)ethylferrocene]palladium (II), and analogous complexes containing bidentate ligands mentioned hereinbefore with iron, cobalt, nickel, ruthenium, rhodium, osmium, and iridium as the metal component.

Methods for preparing the aforementioned catalysts are known to those skilled in the art. For a description of general synthetic techniques, see *Inorganic Syntheses: Reagents for Transition Metal Complex and Organometallic Systems;* R. J. Angelici, Ed., Wiley-Interscience: New York, 1990, Vol. 28, pp. 77–135 (Chapter 2), incorporated herein by reference, wherein representative preparations of Group 8 complexes containing chelating amine, phosphine, and arsine ligands are taught.

As an alternative embodiment of this invention, the catalyst may be anchored or supported on a catalyst support, including a refractory oxide, such as silica, alumina, titania, or magnesia; or an aluminosilicate clay, or molecular sieve or zeolite; or an organic polymeric resin.

Heretofore, the transition metal catalyst has been described as comprising a transition metal and a chelating ligand. It is not precisely known, however, whether the chelating ligand is bound to the transition metal during the entire process of this invention or whether the chelating ligand is in a labile or non-bonded configuration relative to the transition metal during part or all of the process. Generally, it is believed that the chelating ligand is bonded through the Group 15 element to the transition metal; however, such a theory should not be binding upon the invention in any manner. Modern analytical techniques, such as nuclear magnetic resonance spectroscopy ($^{13}$C, $^{1}$H, $^{31}$P), infrared and Raman spectroscopies, and X-ray diffraction, may assist in the determination of initial catalyst structure and changes in structure throughout the process.

The transition metal catalyst may be synthesized first and thereafter employed in the amination process. Alternatively, the catalyst can be prepared in situ in the amination reaction mixture. If the latter method is employed, then a Group 8 catalyst precursor compound and the desired chelating ligand are independently added to the amination reaction mixture wherein formation of the transition metal amination catalyst occurs in situ. Suitable precursor compounds include alkene and diene complexes of the Group 8 metals, preferably, (dibenzylidene)acetone (dba) complexes of the Group 8 metals, as well as, monodentate phosphine complexes of the Group 8 metals, and Group 8 carboxylates. In the presence of the chelating ligand, such as DPPF or BINAP, in situ formation of the transition metal catalyst occurs. Non-limiting examples of suitable precursor compounds include [bis-(dibenzylidene)acetone]palladium (0), tetrakis-(triphenylphosphine)-palladium (0), tris-[(dibenzylidene)acetone]palladium (0), tris-[(dibenzylidene)acetone]dipalladium (0), palladium acetate, and the analogous complexes of iron, cobalt, nickel, ruthenium, rhodium, osmium, iridium, and platinum. Any of the aforementioned catalyst precursors may include a solvent of crystallization. Group 8 metals supported on carbon, preferably, palladium on carbon, can also be suitably employed as a precursor compound. Preferably, the catalyst precursor compound is bis-[(dibenzylidene)acetone]palladium (0).

The quantity of transition metal catalyst which is employed in the process of this invention is any which promotes the formation of the organic amine product having at least one unsaturated moiety. Generally, the quantity is a catalytic amount, which means that the catalyst is used in an amount which is less than stoichiometric relative to the unsaturated organic sulfonate. Typically, the transition metal catalyst ranges from about 0.01 to about 20 mole percent, based on the number of moles of unsaturated organic sulfonate used. Preferably, the quantity of transition metal catalyst ranges from about 1 to about 10 mole percent, and more preferably, from about 3 to about 8 mole percent, based on the moles of unsaturated sulfonate.

The process described herein may be conducted in any conventional reactor designed for catalytic processes. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the organic sulfonate, reactant amine, base, and catalyst are mixed in batch, optionally with a solvent, and the resulting mixture is maintained at a temperature and pressure sufficient to prepare the organic amine having at least one unsaturated group.

Any solvent can be used provided that it does not interfere with the formation of the product amine. Both aprotic and protic solvents are acceptable. Suitable aprotic solvents include, but are not limited to, aromatic hydrocarbons, such as toluene and xylene; chlorinated aromatic hydrocarbons, such as dichlorobenzene; and ethers, such as tetrahydrofuran. Suitable protic solvents include, but are not limited to, water and aliphatic alcohols, such as ethanol, isopropanol, and cyclohexanol, as well as glycols and other polyols. The amount of solvent which is employed may be any amount, preferably, an amount sufficient to solubilize at least in part the unsaturated organic sulfonate, reactant amine, and base. A suitable quantity of solvent typically ranges from about 1 to about 100 grams solvent per gram unsaturated organic sulfonate. Other quantities of solvent may also be suitable, as determined by the specific process conditions and by the skilled artisan.

Generally, the reagents may be mixed together or added to a solvent in any order. Under the basic process conditions electron deficient aryl sulfonates, such as the triflates derived from 4-hydroxybenzophenone and 4-hydroxybenzonitrile, may exhibit some sulfonate cleavage to form phenol. This problem can be avoided by slowly adding the organic sulfonate to a solution of the catalyst, amine, and base, as opposed to mixing the reagents all at once.

No special effort is required to eliminate air from the reaction mixture, unless one or more of the reagents are particularly air-sensitive. If it is desirable or necessary to remove air, the solvent and reaction mixture can be sparged with a non-reactive gas, such as nitrogen, helium, or argon. The process conditions can be any operable conditions which yield the desired amine product. Beneficially, the reaction conditions for this process are mild. For example, a preferred temperature ranges from about ambient, taken as about 22° C., to about 150° C., and preferably, from about 80° C. to about 110° C. The process may be run at subatmospheric or superatmospheric pressures if necessary, but typically proceeds sufficiently well at about atmospheric pressure. The process is generally run for a time sufficient to convert as much of the unsaturated organic sulfonate to product amine as possible. Typical reaction times range from about 30 minutes to about 24 hours, but longer times may be used if necessary.

When an unsaturated organic sulfonate is contacted with a reactant amine in the presence of a base and the transition metal catalyst as described hereinabove, a product amine is produced containing at least one unsaturated organic moiety, represented as 4 in Equation I hereinabove. The product amine may be a primary, secondary, or tertiary amine. The groups $R^1$, $R^2$, and $R^3$ in product amine 4 are identical to those described hereinabove in connection with the unsaturated organic sulfonate and the reactant amine. Preferably, in the product amine of formula 4, $R^1$ is a $C_{2-20}$ vinyl, a $C_{5-15}$ aryl, or a $C_{4-15}$ nitrogen, oxygen, or sulfur-containing heteroaryl group, and $R^2$ and $R^3$ are each independently selected from the group consisting of hydrogen, $C_{1-20}$ alkyl, $C_{4-8}$ cycloalkyl, $C_{6-15}$ aryl groups. Alternatively, $R_2$ and $R_3$ together with the nitrogen atom of the amine can form a $C_{4-15}$ saturated or unsaturated heterocycle. Non-limiting examples of product amines include N-(2-naphthyl)piperidine, 1-(4-methylphenyl)piperidine, 4-methoxydiphenylamine, 4-phenyldiphenylamine, N-methyl, N-phenyl-4-aminobenzophenone, N-(2-methylphenyl)aniline, N-phenyl-2-naphthylamine, N-isobutyl-4-methylaniline, N-butyl-2-methylaniline, N-(2-naphthyl)morpholine, N-isobutyl-2-naphthylamine, N-(biphenyl)butylamine, N-(4-biphenyl)piperidine, N-(4-cyanophenyl)morpholine, N-butyl-4-aminobenzonitrile, and N-butyl-4-aminobenzophenone.

The product amine 4 can be recovered by conventional methods known to those skilled in the art, including, for example, distillation, crystallization, sublimation, and gel chromatography. The yield of product amine will vary depending upon the specific catalyst, reagents, and process conditions used. For the purposes of this invention, "yield" is defined as the mole percentage of amine product recovered, based on the number of moles of unsaturated organic sulfonate employed. Typically, the yield of product amine is greater than about 25 mole percent. Preferably, the yield of product amine is greater than about 60 mole percent, and more preferably, greater than about 80 mole percent.

In another aspect of this invention, arylamines can be advantageously prepared from phenols. In this process, the phenol is first converted to an aryl sulfonate, and then the aryl sulfonate is converted to an arylamine by the catalytic process described hereinbefore. Aryl sulfonates are readily prepared by reacting a phenol with a sulfonating agent, as described in the following references: P. J. Stang, M. Hanack, and L. R. Subramanian, *Synthesis* 1982, 85; J. K. Stille, *Angewante Chemie* 1986, 25, 504, *Angewante Chemie, Int. Ed. Engl,* 1986, 25, 508, incorporated herein by reference.

The phenol can be characterized as any molecule comprising a phenyl ring substituted with a hydroxyl group. The phenol can be a monocyclic ring system, such as unsubstituted phenol; a ring assembly, such as hydroxybiphenyl, or a fused ring system, such as naphthol. The phenol can be substituted with one or more inert substituents, similar to those described hereinbefore for the unsaturated organic sulfonate (1). Phenols which can be beneficially employed include, but are not limited to, unsubstituted phenol, cresol, xylenol, methylisopropylphenol, naphthol, anthrol, phenanthrol, hydroxybiphenyl, and the like. Preferably, the phenol is a $C_{6-15}$ phenol or a substituted derivative thereof, preferably, an alkyl-substituted derivative thereof. Suitable sulfonating agents include alkyl and aryl sulfonyl chlorides, alkyl and aryl sulfonic acids, and alkyl and aryl sulfonic anhydrides. Examples of preferred sulfonating agents include trifluoromethane sulfonyl chloride, triflic acid, triflic anhydride, tosyl chloride, toluene sulfonic acid, and toluene sulfonic anhydride. Sulfonating conditions are mild. Typical temperatures range from about −20° C. to about 100° C. A tertiary amine, such as triethylamine, may be needed to activate the reaction.

The invention will be further clarified by a consideration of the following examples, which are intended to be purely exemplary of the use of the invention. Other embodiments of the invention will be apparent to those skilled in the art from a consideration of this specification or practice of the invention as disclosed herein. Unless otherwise noted, all percentages are given on a mole percent basis. All reagents were purchased from commercial suppliers and used without further purification. Tetrahydrofuran (THF) and toluene were distilled from sodium benzophenone ketyl under nitrogen.

Dichloro-[1,1'-bis(diphenylphosphino)ferrocene] palladium (II), (DPPF)PdCl$_2$, was prepared by standard addition of phosphine to dichloro-bis(acetonitrile)palladium (II), formed by refluxing palladium (II) chloride in acetonitrile. See, for example, T. Hayashi et al., *Tetrahedron Letters,* No. 21, 1979, 1871–1874, incorporated herein by reference. Bis-(dibenzylideneacetone)palladium (0), Pd(dba)$_2$, was prepared by the method described by M. F. Rettig and P. M. Maitlis in *Inorganic Syntheses* 1992, 28, 110, incorporated herein by reference.

The aryl triflates were prepared according to general methods of Stille (A. M. Echavarren and J. K. Stille, *Journal of the American Chemical Society,* 1987, 109, 5478–5486). 4-Methoxyphenyl triflate was prepared by the Stille method, *Journal of the American Chemical Society,* ibid. 2-Naphthyl triflate was prepared by the method of P. J. Stang et al.

(*Synthesis* 1982, 85–126). 4-Cyanophenyl triflate was prepared by the method of W. Carbri et al. (*Journal of Organic Chemistry* 1992, 57, 1481–1486). 4-Benzoylphenyl triflate was prepared by the method of K. Kotsuki et al. (*Synthesis* 1990, 1145). 4-Phenylphenyl triflate was prepared by the method of D. Badone et al. (*Tetrahedron Letters* 1994, 30, 5477–5480). 2-Methylphenyl triflate was prepared by the method of H. K. Reuter et al. (*Journal of Organic Chemistry* 1993, 58, 4722–4726). All of the aforementioned citations and methods described therein are incorporated herein by reference.

Reactions were set-up in an inert atmosphere glove box or by using standard Schlenk or vacuum line techniques. Amines were added by syringe without degassing with the exception of aniline, which was distilled under nitrogen. $^1$H and $^{13}$C{$^1$H}NMR spectra were obtained on a GE QE 300 MHz, GEΩ300 MHz, or Brucker AM500 MHz Fourier Transform spectrometer. $^1$H and $^{13}$C{$^1$H}NMR spectra were recorded relative to residual protiated solvent. A positive value of the chemical shift denotes a resonance downfield from tetramethylsilane (TMS). Standard elemental analyses were performed on each product. GC analyses were conducted on a Hewlett Packard 5890 instrument connected to a 3395 integrator.

EXAMPLE 1

Representative example of Method A: N-(2-naphthyl) piperidine

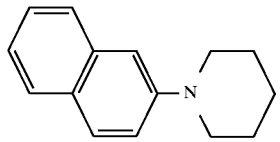

The method described in this example is representative of method "A". Into a screw-capped test tube were weighed 8.6 mg (0.015 mmol) Pd(dba)$_2$, 12.8 mg (0.023 mmol) DPPF, and 44.3 mg (0.462 mmol) sodium t-butoxide (NaO-t-Bu). The solid materials were suspended in 8 ml of toluene. 2-Naphthyltriflate (85.0 mg, 0.308 mmol) was dissolved in 1 ml of toluene and added to the test tube. The test tube was sealed with a cap containing a polytetrafluoroethylene (PTFE) septum and removed from the dry box. Piperidine (40.0 μl, 0.462 mmol) was added to the test tube by syringe. The reaction mixture was heated at 105° C. for 5 hours. Thin layer chromatography (TLC) of the reaction mixture indicated complete consumption of the naphthyltriflate. The reaction mixture was cooled to room temperature, and the volatile materials were removed by rotary evaporation. Sublimation (120° C., 0.1 torr) of the resulting residue afforded N-(2-naphthyl)piperidine as a white solid (50.0 mg, 77% yield).

EXAMPLE 2

Representative example of Method B: 1-(4-methylphenyl) piperidine

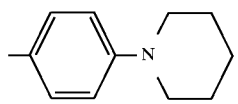

This example is representative of procedure "B". Into a screw-capped test tube were weighed 29 mg (0.052 mmol) Pd(dba)$_2$, 55 mg (0.10 mmol) DPPF, and 144 mg (1.5 mmol) NaO-t-Bu. The solid materials were suspended in 12 ml of toluene. 4-Methylphenyltriflate (240 mg, 1.0 mmol) was dissolved in 1 ml of toluene and added to the test tube. The test tube was sealed with a cap containing a PTFE septum and removed from the dry box. Piperidine (148 μl, 1.5 mmol) was added to the test tube by syringe. The reaction mixture was heated at 100° C. for 5 hours. TLC of the reaction mixture indicated complete consumption of the starting triflate. The reaction mixture was cooled to room temperature, and the mixture was absorbed onto silica gel. Chromatography on a silica gel column using 50:1 hexanes-:diethyl ether afforded 1-(4-methylphenyl)piperidine as a clear oil. (135 mg, 77% yield).

EXAMPLE 3

Representative example for aminations with aniline: 4-methoxydiphenylamine

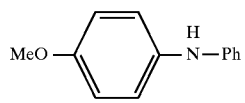

This example is representative of amination examples using aniline. Into a screw-capped test tube were weighed 2.0 mg (0.0038 mmol) Pd(dba)$_2$, 6.0 mg (0.011 mmol) DPPF, and 33.6 mg (0.350 mmol) NaO-t-Bu. The solid materials were suspended in 8 ml of toluene. 4-Methoxyphenyltriflate (56.7 mg, 0.221 mmol) was dissolved in 1 ml of toluene and added to the test tube. Aniline (30.0 μl, 0.329 mmol) was added, and the test tube was sealed with a cap containing a PTFE septum. The reactions were stirred in an 85° C. oil bath for 8 hours. After this time, the volatile materials were removed under vacuum and 4-methoxydiphenylamine was collected by sublimation (110° C., 0.05 torr) as a white solid (41 mg, 94%).

EXAMPLE 4

4-Phenyldiphenylamine

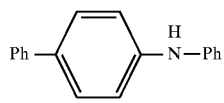

Using the general procedure for anilines with 68.4 mg (0.226 mmol) 4-biphenyltriflate and 30.0 μl (0.329 mmol) of aniline yielded 4-phenyl-diphenylamine as a white solid (55 mg, 99%).

EXAMPLE 5

N-Methyl, N-phenyl-4-aminobenzophenone

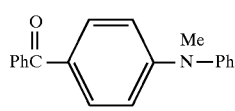

The general procedure B using 49.9 mg (0.151 mmol) of 4-benzophenone-triflate and 24.7 μl (0.227 mmol) of N-methylaniline gave 55% yield of N-Methyl, N-phenyl-4-aminobenzophenone after silica gel chromatograph using 5% ethyl acetate in hexanes.

EXAMPLE 6

N-(2-Methylphenyl)aniline

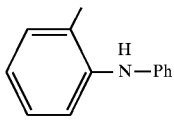

The general procedure B using 51.7 mg (0.215 mmol) of o-tolyltriflate and 29.4 μl (0.323 mmol) of aniline gave 95% yield of N-(2-methylphenyl)aniline after sublimation (130° C., 0.1 torr).

EXAMPLE 7

N-Phenyl-2-naphthylamine

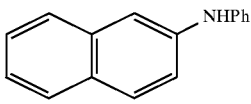

Using the general procedure for anilines with 66.8 mg (0.242 mmol) of 2-naphthyltriflate and 30.0 μl (0.329 mmol) of aniline yielded N-phenyl-2-naphthylamine as a white solid (52 mg, 98%), whose NMR spectra were identical to commercial material available from Aldrich.

EXAMPLE 8

N-Phenyl-2-naphthylamine

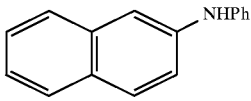

Into a screw-capped test tube were weighed 2.2 mg (0.0038 mmol) Pd(dba)$_2$, 4.0 mg (0.0064 mmol) BINAP, 34.7 mg (0.361 mmol) NaO-t-Bu, and 70.0 mg (0.253 mmol) 2-naphthyltriflate. The solid materials were suspended in 8 ml of toluene. Aniline (33.0 μl, 0.362 mmol) was added to the mixture, and the test tube was sealed with a cap containing a PTFE septum. The reaction was stirred at 85° C. for 6 hours. The volatile materials were removed under vacuum, and N-phenyl-2-naphthylamine was collected by sublimation (110° C., 0.05 torr) as a white solid (53 mg, 96%).

EXAMPLE 9

N-Phenyl-2-naphthylamine

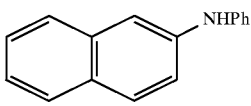

The general procedure for anilines with 66.8 mg (0.242 mmol) of 2-naphthyltriflate and 30.0 μl (0.329 mmol) of aniline, but in 8 ml of THF solvent, gave 40 mg (76%) of N-phenyl-2-naphthylamine.

EXAMPLE 10

N-Isobutyl-4-methylaniline

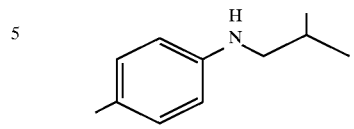

Using the general procedure B with 120 mg (0.50 mmol) of 4-methylphenyltriflate and 75 ml (0.75 mmol) of isobutylamine gave N-isobutyl-4-methylaniline as a pale yellow oil (37 mg, 45%).

EXAMPLE 11

N-Isobutyl-4-methylaniline

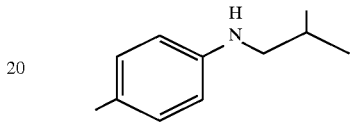

Into a screw-capped test tube were weighed 10 mg (0.017 mmol) of Pd(dba)$_2$, 21 mg (0.034 mmol) of BINAP, and 50 mg (0.65 mmol) of NaO-t-Bu. The solid materials were suspended in 8 ml of toluene. 4-Methylphenyltriflate (80 mg, 0.33 mmol) was dissolved in 1 ml of toluene and added to the test tube. The test tube was sealed with a cap containing a PTFE septum and removed from the dry box. Isobutylamine (50.0 μl, 0.50 mmol) was added to the test tube by syringe. The reaction mixture was heated at 100° C. for 3 hours. A TLC of the reaction mixture indicated complete consumption of the starting triflate. The reaction mixture was cooled to room temperature, and the mixture was absorbed onto silica gel. Chromatography on a silica gel column using 30:1 hexanes:diethyl ether afforded N-Isobutyl-4-methylaniline as a pale yellow oil (35 mg, 65% yield).

EXAMPLE 12

N-Butyl-2-methylaniline

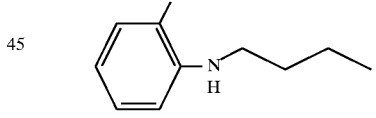

General procedure B using 55.1 mg (0.229 mmol) of o-tolyltriflate and 34.0 μl (0.344 mmol) of n-butylamine gave 67% yield of N-butyl-2-methylaniline after silica gel chromatograph using 5% ethyl acetate in hexanes.

EXAMPLE 13

4-(2-Naphthyl)morpholine

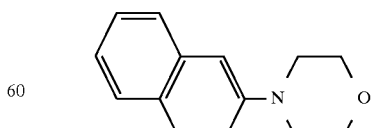

General procedure A with 50.0 mg (0.181 mmol) of 2-naphthyltriflate and 24.0 μl (0.272 mmol) of morpholine gave 4-(2-naphthyl)morpholine as a white solid (35 mg, 91% yield).

EXAMPLE 14

N-Isobutyl-2-napthylamine

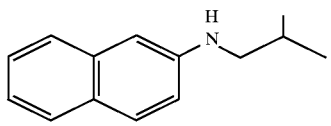

General procedure B with 23.0 mg (0.083 mmol) of 2-naphthyltriflate and 9.9 μl (0.10 mmol) of isobutylamine gave 72% yield of N-isobutyl-2-naphthylamine after silica gel chromatograph using 5% ethyl acetate in hexanes. High resolution mass spectroscopy (HRMS) calculated for $C_{14}H_{17}N$ ($M^+$): 199.1361. Found: 199.1361 Anal. Calc'd. for $C_{14}H_{17}N$: C, 84.37; H, 8.60; N, 7.03. Found: C, 84.13; H, 8.40; N, 6.85.

EXAMPLE 15

N-(Biphenyl)butylamine

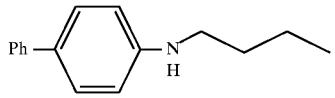

General procedure B with 50.0 mg (0.166 mmol) of 4-biphenyltriflate and 24.5 μl (0.249 mmol) of butylamine gave N-(biphenyl)butylamine as a pale yellow oil (19 mg, 50% yield). HRMS calculated for $C_{16}H_{19}N$ ($M^+$): 225.1518. Found: 225.1516 Anal. Calc'd. for $C_{16}H_{19}N$: C, 85.29; H, 8.5; N, 6.22. Found: C, 85.14, H, 8.66, N, 5.99.

EXAMPLE 16

N-(4-Biphenyl)piperidine

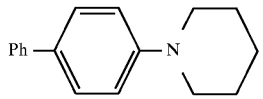

Using general procedure B with 150 mg (0.50 mmol) of 4-biphenyltriflate and 79.0 μl (0.75 mmol) of piperidine gave N-(4-biphenyl)piperidine as a white solid (79 mg, 67% yield). HRMS calculated for $C_{17}H_{19}N$ ($M^+$): 237.1518. Found: 237.1517. Anal. Calc'd for $C_{17}H_{19}N$: C, 86.03; H, 8.07; N, 5.9. Found: C, 85.94, H, 8.27, N, 5.75.

EXAMPLE 17

N-(4-Cyanophenyl)morpholine

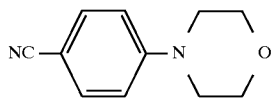

General procedure A with 50.0 mg (0.199 mmol) of 4-cyanophenyltriflate and 26.0 μl (0.299 mmol) of morpholine gave N-(4-cyanophenyl)morpholine as a white solid (31 mg, 82% yield).

EXAMPLE 18

N-Butyl-4-aminobenzonitrile

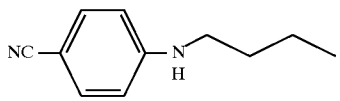

General procedure B using 62.4 mg (0.248 mmol) of 4-cyanophenyltriflate and 36.8 μl (0.373 mmol) of n-butylamine gave 95% yield of N-butyl-4-aminobenzonitrile after silica gel chromatography using a gradient of 5 to 15% ethyl acetate in hexanes.

EXAMPLE 19

N-sec-Butyl-4-cyanoaniline

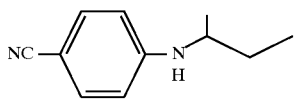

Using general procedure B with 50.0 mg (0.199 mmol) of 4-cyanophenyltriflate and 29.5 μl (0.299 mmol) of isobutylamine gave N-sec-butyl-4-cyanoaniline as a pale yellow oil (26 mg, 74% yield). HRMS calc'd for $C_{11}H_{14}N_2$: 174.1157. Found: 174.1156.

EXAMPLE 20

N-Butyl-4-aminobenzophenone

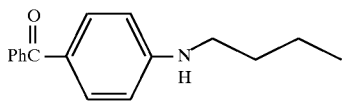

The general procedure B using 62.3 mg (0.188 mmol) of 4-benzophenonetriflate and 28.0 μl (0.283 mmol) of n-butylamine gave 84% yield of N-butyl-4-aminobenzophenone after silica gel chromatograph using a gradient 5 to 10% ethyl acetate in hexanes.

What is claimed is:

1. A process of preparing an organic amine containing at least one unsaturated organic group, the process comprising contacting an unsaturated organic sulfonate with a reactant amine in the presence of a base and a transition metal catalyst under reaction conditions sufficient to prepare an organic amine containing at least one unsaturated organic group, the transition metal catalyst comprising a Group 8 metal and at least one chelating ligand selected from the group consisting of unsaturated Group 15 heterocycles, Group 15-substituted arylenes, Group 15-substituted metallocenes, and Group 15-substituted alkanes.

2. The process of claim 1 wherein the unsaturated organic sulfonate is represented by the formula:

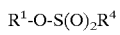

wherein R is a $C_{2-20}$ vinyl, a $C_{5-15}$ aryl, or a $C_{4-15}$ nitrogen, oxygen, or sulfur-containing heteroaryl group, and wherein $R^4$ is a $C_{1-10}$ alkyl, $C_{1-10}$ perfluoroalkyl, a $C_{6-15}$ aryl, or $C_{6-15}$ alkaryl group.

3. The process of claim 1 wherein $R^1$ is selected from the group consisting of phenyl, cyclopentadienyl, biphenylyl, terphenylyl, naphthyl, indenyl, anthryl, phenanthryl, azulenyl, fluorenyl, and phenalenyl, furyl, pyranyl, isobenzofuranyl, xanthenyl, pyridyl, pyrazinyl, pyrimidinyl, pyrrolyl, indolizinyl, isoquinolyl, quinolyl, thienyl, benzothienyl, naphthothienyl, and thianthrenyl.

4. The process of claim 1 wherein the unsaturated organic sulfonate is a $C_{5-15}$ aryl triflate or $C_{4-15}$ heteroaryl triflate.

5. The process of claim 1 wherein the reactant amine is represented by the formula:

$$HNR^2R^3$$

wherein $R^2$ and $R^3$ are each independently selected from the group consisting of hydrogen, $C_{1-20}$ alkyl, $C_{4-8}$ cycloalkyl, and $C_{6-15}$ aryl groups or wherein $R^2$ and $R^3$ together with the nitrogen atom of the amine form a $C_{4-15}$ saturated or unsaturated heterocycle.

6. The process of claim 1 wherein the amine is selected from the group consisting of ammonia, ethylamine, propylamine, n-butylamine, t-butylamine, pentylamine, hexylamine, cyclohexylamine, octylamine, 2-ethylhexylamine, dipropylamine, dibutylamine, dicyclohexylamine, cyclohexylethylamine, aniline, toluidine, dimethylaniline, isopropylaniline, N-methylaniline, N,N-diphenylamine, morpholine, isoindoline, indoline, piperazine, piperidine, pyrazoline, pyrazolidine, imidazoline, imidazolidine, pyrroline, pyrrolidine, phenoxazine, carbazole, purine, indole, isoindole, pyrrole, pyrazole, and imidazole.

7. The process of claim 1 wherein the sulfonate and reactant amine functionalities are bound to the same molecule and the process occurs intramolecularly.

8. The process of claim 1 wherein the molar ratio of reactant amine to unsaturated organic sulfonate ranges from about 1/1 to about 10/1.

9. The process of claim 1 wherein the base is selected from the group consisting of alkali metal hydroxides, alkali metal alkoxides, metal carbonates, alkali metal amides, alkali metal aryl oxides, tertiary amines, tetraalkylammonium hydroxides, and diaza organic bases.

10. The process of claim 1 wherein the molar ratio of base to unsaturated organic sulfonate ranges from about 1/1 to about 3/1.

11. The process of claim 1 wherein the Group 8 transition metal is palladium, platinum, or nickel.

12. The process of claim 1 wherein the chelating Group 15-substituted arylene is a chelating Group 15-substituted $C_{4-20}$ arylene.

13. The process of claim 12 wherein the Group 15-substituted arylene is 1,1'-bis(diphenylphosphino)-2,2'-binaphthyl (BINAP) or 1,1'-bis(di-p-tolylphosphino)-2-2'-binaphthyl (Tol-BINAP).

14. The process of claim 1 wherein the chelating ligand is a Group 15-substituted metallocene of iron, titanium, vanadium, chromium, manganese, cobalt, nickel, molybdenum, or ruthenium.

15. The process of claim 14 wherein the Group 15-substituted metallocene is a Group 15-substituted ferrocene.

16. The process of claim 15 wherein the Group 15-substituted ferrocene is 1,1'-bis(diphenylphosphino) ferrocene (DPPF).

17. The process of claim 1 wherein the chelating Group 15-substituted alkane is a chelating dialkyl or diaryl Group 15-substituted $C_{2-5}$ alkane or a hybrid thereof.

18. The process of claim 1 wherein the chelating ligand is an unsaturated $C_{5-15}$ nitrogen heterocycle.

19. The process of claim 1 wherein the transition metal catalyst is represented by the formula:

$$(LL)_{1 \text{ or } 2}MX_y$$

wherein (LL) is the chelating ligand, M is the Group 8 transition metal, each X is independently a monovalent or divalent anionic ligand; and wherein y varies from 0 about 4.

20. The process of claim 19 wherein the transition metal catalyst is selected from the group consisting of dichloro-[1,1'-bis(diphenylphosphino)ferrocene]palladium (II), dichloro-[1,1'-bis(diphenylphosphino)-2,2'-binaphthyl] palladium (II), dichloro-[1,2-bis (diphenylarsino)benzene] platinum (II), 1,2-bis (diphenylphosphino)benzene]platinum (II) acetate, dichloro-[1-diphenylphosphino-2-(1-dimethylamino)ethylferrocene]palladium (II).

21. The process of claim 1 wherein the catalyst is prepared in situ in the amination reaction mixture.

22. The process of claim 21 wherein the catalyst is prepared from an alkene or diene complex of a Group 8 transition metal complex or a Group 8 transition metal carboxylate combined with 1,1'-bis(diphenylphosphino) ferrocene or 1,1'-bis(diphenylphosphino)-2,2'-binaphthyl.

23. The process of claim 22 wherein the alkene complex of the Group 8 transition metal is (dibenzylidene)acetone.

24. The process of claim 1 wherein the catalyst is anchored or supported on a catalyst support.

25. The process of claim 1 wherein a solvent is employed selected from the group consisting of aromatic hydrocarbons, chlorinated aromatic hydrocarbons, ethers, water, and aliphatic alcohols.

26. The process of claim 1 wherein the process conditions include a temperature ranging from about 22° C. to about 150° C.

27. The process of claim 1 wherein the organic amine product is represented by the formula:

$$R^1NR^2R^3$$

wherein $R^1$ is a $C_{2-20}$ vinyl, a $C_{5-15}$ aryl, or a $C_{4-15}$ nitrogen, oxygen, or sulfur-containing heteroaryl group, and wherein $R^2$ and $R^3$ are each independently selected from the group consisting of hydrogen, $C_{1-20}$ alkyl, $C_{4-8}$ cycloalkyl, $C_{6-15}$ aryl groups, or wherein $R_2$ and $R_3$ together with the nitrogen atom of the amine form a $C_{4-15}$ saturated or unsaturated heterocycle.

28. The process of claim 1 wherein the yield of organic amine is at least about 60 mole percent.

29. A process of preparing an organic amine containing at least one unsaturated organic group, the process comprising contacting an organic sulfonate having the formula:

$$R^1\text{-O-S(O)}_2R^4$$

wherein $R^1$ is a $C_{2-20}$ vinyl, $C_{5-15}$ aryl, or $C_{4-15}$ nitrogen, oxygen, or sulfur-containing heteroaryl group and wherein $R^4$ is a $C_{1-10}$ alkyl, $C_{1-10}$ perfluoroalkyl, or $C_{6-15}$ aryl or alkaryl group, with a reactant amine represented by the formula:

$$HNR^2R^3$$

wherein $R^2$ and $R^3$ are each independently selected from the group consisting of hydrogen, $C_{1-20}$ alkyl, $C_{4-8}$ cycloalkyl, and $C_{5-15}$ aryl groups or wherein $R^2$ and $R^3$ together with the nitrogen atom of the amine form a $C_{4-15}$ saturated or unsaturated heterocycle, the contacting occurring in the presence of a base and a catalytic amount of a transition metal catalyst at a temperature ranging from about 22° C. to about 150° C. so as to produce an organic amine represented by the formula:

$R^1NR^2R^3$ wherein $R^1$, $R^2$ and $R^3$ are as defined hereinabove, the transition metal catalyst comprising a Group 8 metal selected from nickel, palladium, or platinum and at least one chelating ligand which is 1,1'-bis(diphenylphosphino) ferrocene or 1,1'-bis(diphenylphosphino)-2,2'-binaphthyl.

30. A process of preparing an arylamine comprising (a) contacting a phenol with a sulfonating agent under reaction conditions sufficient to prepare an aryl sulfonate, and thereafter (b) contacting the aryl sulfonate with a reactant amine in the presence of a base and a transition metal catalyst under reaction conditions sufficient to prepare the arylamine, the transition metal catalyst comprising a Group 8 metal and at least one chelating ligand selected from the group consisting of unsaturated Group 15 heterocycles, Group 15-substituted arylenes, Group 15-substituted metallocenes, and Group 15-substituted alkanes.

31. The process of claim 30 wherein the phenol is a $C_{6-15}$ phenol or substituted derivative thereof and wherein the sulfonating agent is selected from the group consisting of alkyl and aryl sulfonic acids, alkyl and aryl sulfonic anhydrides, and alkyl and aryl sulfonic chlorides.

* * * * *